United States Patent

[11] 4,390,535
[45] Jun. 28, 1983

Yamada et al.

[54] ANTIMICROBIAL 7-(α-ACYLAMINO-α-ARYLACETAMIDO)-3-(SUBSTITUTED METHYL)CEPHALOSPORIN COMPOUNDS

[75] Inventors: Hirotada Yamada, Nishinomiya; Kiyokazu Jimpo, Moriguchi; Takao Okuda, Toyonaka; Hiroshi Noguchi, Ashiya; Hisao Tobiki, Kobe, all of Japan

[73] Assignee: Sumitomo Chemical Company, Ltd., Osaka, Japan

[21] Appl. No.: 240,666

[22] Filed: Mar. 5, 1981

[30] Foreign Application Priority Data

Mar. 5, 1980 [JP] Japan ............................ 55-28536
Mar. 5, 1980 [JP] Japan ............................ 55-28537

[51] Int. Cl.³ .................. A61K 31/545; C07D 501/56
[52] U.S. Cl. .................................. 424/246; 544/27
[58] Field of Search .......................... 544/27; 424/246

[56] References Cited

U.S. PATENT DOCUMENTS

| 4,068,074 | 1/1978 | Murakami et al. | 544/27 |
| 4,080,498 | 3/1978 | Numata et al. | 544/27 |
| 4,156,724 | 5/1979 | Yamada et al. | 424/246 |
| 4,165,373 | 8/1979 | Yamada et al. | 544/27 |

FOREIGN PATENT DOCUMENTS

| 49-70990 | 7/1974 | Japan . |
| 50-131981 | 10/1975 | Japan . |
| 50-157390 | 12/1975 | Japan . |
| 51-88988 | 8/1976 | Japan . |
| 54-16496 | 2/1979 | Japan . |
| 55-49385 | 4/1980 | Japan . |

Primary Examiner—Paul M. Coughlan, Jr.
Attorney, Agent, or Firm—Sughrue, Mion, Zinn, Macpeak and Seas

[57] ABSTRACT

Compounds of the formula

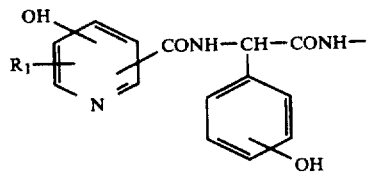

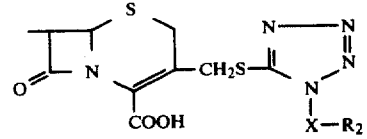

wherein $R_1$ is hydrogen or a ($C_1$–$C_4$) alkyl group, X is a straight or branched chain $C_1$–$C_4$ alkylene group and $R_2$ is a carboxyl group or a sulfo group; and the pharmaceutically acceptable salts thereof exhibit strong inhibitory activities against a wide variety of Gram-positive and Gram-negative bacteria including *Psendomonas aeruginosa, indolepositive Proteus* and *Enterobacter aerogenes,* and also have an increased and prolonged serum level in a living body. The compounds are therefore useful as antibacterial agents for the treatment of infectious diseases caused by Gram-positive and Gram-negative bacteria.

3 Claims, No Drawings

ANTIMICROBIAL 7-(α-ACYLAMINO-α-ARYLACETAMIDO)-3-(SUBSTITUTED METHYL)CEPHALOSPORIN COMPOUNDS

FIELD OF THE INVENTION

The present invention relates to cephalosporin compounds. More particularly, it pertains to antimicrobial 7-(α-acylamino-α-arylacetamido)-3-(substituted methyl)cephalosporin compounds, and their composition and use, and to a process for producing the same.

BACKGROUND OF THE INVENTION

The cephalosporin compounds provided by the present invention are those represented by the formula:

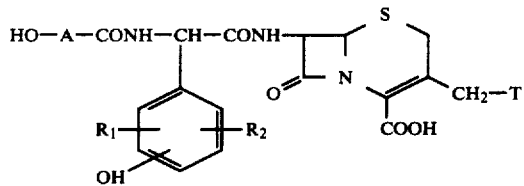

wherein HO-A- represents a hydroxypyridyl group which may further be substituted with a lower alkyl group, a lower alkoxy group, a lower alkanoyl group, a lower alkoxycarbonyl group, a lower alkylmercapto group, a mercapto group, a hydroxyl group, a lower alkoxymethyl group, a halogen atom, a cyano group, a nitro group, a lower alkylsulfonyl group, an arylsulfonyl group, a sulfamoyl group, a carbamoyl group, an aryloxycarbonylamino group, an acetoacetylamino group, a lower alkylamino group, a lower dialkylamino group, a halogenoalkyl group, an alkenyl group, an aryl group, a cycloalkyl group and a condensed ring cyclo(-lower)alkylene group; $R_1$ and $R_2$ may be the same or different and each represents a substituent selected from the group consisting of a hydrogen atom, a dialkylamino group, a hydroxyl group, an alkanoyloxy group, a lower alkyl group, a lower alkoxyl group, a halogen atom and a hydroxymethyl group; T represents a group of either one of the formulae:

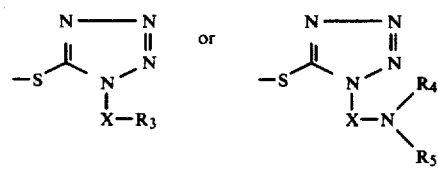

wherein $R_3$ represents a carboxyl group or a sulfo group, X represents a straight chain or branched chain alkylene group, $R_4$ and $R_5$ may be the same or different and each represents a lower alkyl group; and their pharmaceutically acceptable non-toxic salts.

The present invention also provides antimicrobial compositions comprising an antimicrobially effective amount of the cephalosporin compound of the formula (I) or its pharmaceutically acceptable non-toxic salt and a carrier or diluent. It further provides a process for producing the cephalosporin compound of the formula (I).

DETAILED DESCRIPTION OF THE INVENTION

The compounds of the present invention represented by the formula (I) and non-toxic salts thereof exhibit a strong antimicrobial activity against gram-positive and gram-negative bacteria including various microorganisms to which many of the commercially available cephalosporin type antibiotics are not effective, for example, Pseudomonas aeruginosa, indole-positive Proteus, Serratia, Enterobacter aerogenes and the like.

Further, the compounds of the invention and non-toxic pharmaceutically acceptable salts thereof have a good water-solubility and excellent pharmacokinetic properties, such as their increased and prolonged serum level in a living body. Thus, they are useful as antimicrobial agents for preventing and treating various bacterial infections caused by said microorganisms in human and animals including poultry and domestic animals without causing any serious side-effects.

For the treatment or prevention of such infectious diseases, the compounds of this invention, either individually or in combination with a pharmaceutically acceptable carrier or diluent, or another active ingredient(s), e.g., another chemotherapeutic agent(s), can be administered parenterally to a subject.

The dosage of the compounds of the formula (I) of this invention will vary with the body weight, age and conditions of an individual subject, the kind of bacteria, and the pharmacokinetic properties of the particular compounds chosen. Although the particular dosage will be determined by a physician taking these factors into consideration, the compounds of the formula (I) are, in general, most desirably administered parenterally at a dosage ranging from about 5 mg/kg of body weight/day to 150 mg/kg of body weight/day, preferably from 15 mg/kg of body weight/day to 100 mg/kg of body weight/day in a single dose or in multiple doses 2 to 5 times daily.

For parenteral administrations the compounds of this invention may be used in the form of sterile solution or suspension containing additionally a pharmaceutically acceptable diluent or carrier such as water, saline solution, Ringer's solution, glycerin, polyethylene glycol, etc. These preparations or formulations may also contain suitable auxiliary materials, such as stabilizers, buffer substances, wetting agents, emulsifiers, local anesthetics, or salts that regulate the osmotic pressure.

The α-carbon atom in the side chain at the 7-position in the formula (I), i.e., a phenylglycine moiety, is an asymmetric center and the compound of this invention can exist in two optical isomers. The present invention includes in its scope these two isomers (D-diastereomer and L-diastereomer) as well as a DL-form, with a preferred compound being a D-form.

Examples of said pharmaceutically acceptable non-toxic salts of the compounds of the formula (I) are a sodium salt, a potassium salt, a calcium salt, a magnesium salt, a triethylamine salt, a diethanolamine salt, a morpholine salt, a procaine salt, an L-arginine salt, an L-lysine salt and the like.

The cephalosporin compounds of the present invention and the salts thereof can be prepared by reacting a carboxylic acid of the formula (II)

HO-A-COOH  (II)

wherein HO-A- is as defined above, or a reactive derivative thereof, with a compound of the formula (III)

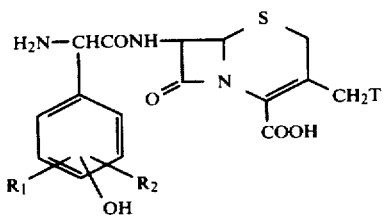

wherein $R_1$, $R_2$ and T are as defined above, or a salt or a derivative of the compound of the formula (III).

Referring more particularly, the reaction between the compound of the formula (II) or a salt or a reactive derivative thereof and the compound of the formula (III) or a salt or a derivative thereof is generally conducted in an inert solvent. Examples of the inert solvents are polar solvents such as dichloromethane, chloroform, acetone, tetrahydrofuran, dioxane, acetonitrile, methyl isobutyl ketone, ethyl alcohol, dimethylformamide, dimethyl sulfoxide, hexamethylphosphoric triamide, sulforane and the like, non-polar solvents such as benzene, toluene, petroleum ether, n-hexane and the like, or a mixture thereof.

The reactive derivative of the carboxylic acid represented by the formula (II) means a reactive derivative of the carboxyl group, for example, an acid halide, an acid anhydride, an acid azolide, an active ester, an acid azide and the like. Examples of the reactive derivatives are mixed acid anhydrides with an acid such as dialkylphosphoric acids, phenylphosphoric acid, diphenylphosphoric acid, dibenzylphosphoric acid, dialkyl phosphorous acids, methanesulfonic acid, toluenesulfonic acid, naphthalenesulfonic acid, alkylcarbonic acids, aliphatic carboxylic acids (e.g., pivalic acid, pentanoic acid, isopentanoic acid, 2-ethylbutanoic acid), aromatic carboxylic acids, or symmetric acid anhydrides; acid azolides with imidazole, substituted imidazoles, dimethylpyrazole, triazole, tetrazole and the like; or active esters such as cyanomethyl ester, methoxymethyl ester, p-nitrophenyl ester, 2,4-dinitrophenyl ester, trichlorophenyl ester, pentachlorophenyl ester, methanesulfonylphenyl ester, phenylthiophenyl ester, p-nitrophenylthio ester, p-cresylthio ester, carboxymethylthio ester, pyranyl ester, pyridyl ester, piperidyl ester, 8-quinolylthio ester and the like; or active esters with N,N'-dimethylhydroxylamine, 1-hydroxy-2(1H)-pyridone, N-hydroxysuccinimide or N-hydroxyphthalimide and the like.

When the carboxylic acid of the formula (II) is used in the form of a free carboxylic acid or a salt thereof, the reaction is preferably conducted in the presence of a condensing agent, for example, N,N'-dicyclohexylcarbodiimide, N-cyclohexyl-N-morpholinoethylcarbodiimide, N-cyclohexyl-N-(4-diethylaminocyclohexyl)carbodiimide, N,N'-diethylcarbodiimide, N,N'-diisopropylcarbodiimide, N-ethyl-N-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide inner salt, (chloromethylene)dimethylammonium chloride and the like.

In this manner, any amidation agents which have generally been used in the fields of peptide chemistry or penicillin and cephalosporin chemistry can be used in preparing the compounds of the formula (I) in the present invention.

The salt of the compound having the formula (III) includes alkali metal or alkaline earth metal salts such as sodium, potassium, calcium salt and the like, organic base salts such as trimethylamine, triethylamine, quinoline, collidine salt and the like, organic sulfonic acid salts such as toluenesulfonic acid, naphthalenesulfonic acid, tetralinsulfonic acid salt and the like, and the derivative of the compound of the formula (III) includes carboxyl derivatives such as those having protected carboxyl groups such as in the form of esterified or amidated carboxyl groups or in the form of acid anhydrides.

The protected carboxyl derivatives are those having a group which is capable of providing easily a carboxylic acid group by cleavage after acylation and preferably those providing a free carboxylic acid by, for example, solvolysis, e.g., hydrolysis or alcoholysis in an acidic or weakly alkaline medium, hydrogenolysis, reduction, oxidation, nucleophilic substitution, photoreaction or enzymatic reaction.

The above-described protected carboxyl derivatives are those having a protective group for carboxylic acid generally used in the field of peptide chemistry or in the field of penicillin and cephalosporin chemistry such as a silyl ester, an organotin ester, a toluenesulfonylethyl ester, a p-nitrobenzyl ester, a benzyl ester, a phenacyl ester, a 2-furylmethyl ester, a diphenylmethyl ester, a substituted diphenylmethyl ester, p-methoxybenzyl ester, a trityl ester, a benzoyloxymethyl ester, a lower alkanoyloxymethyl ester, a dimethylmethyleneamino ester, a p-nitrophenyl ester, a methylsulfonylphenyl ester, a methylthiophenyl ester, a t-butyl ester, a 4-picolyl ester, an iodoethyl ester, a trichloroethyl ester, a phthalimidomethyl ester, a 3,4-dimethoxy- or 3,5-dimethoxybenzyl ester, a 2-nitrobenzyl ester, a 2,2'-dinitrobenzyl ester, an acetyloxycarbonyl group, a trichloroethyl ester,

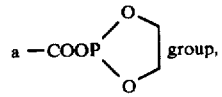

a —COON=CHR' group wherein R' is an alkyl or aryl group,

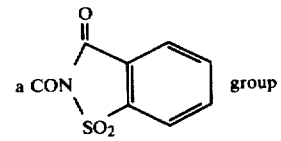

and the like.

The above-described derivatives of the compounds of the formula (III) can be used in the form of salts thereof such as hydrochloride, toluenesulfonates, naphthalenesulfonates, tetralinsulfonates, etc.

In the case where the above derivative used is in the form of a silyl ester, the derivative may have another silyl groups on other moieties which can be silylated, i.e., hydroxy groups, amino groups, etc.

The temperature of the reaction between the carboxylic acid represented by the formula (II) or a reactive derivative thereof and a 7-amino-acylamidocephalosporin represented by the formula (III) or a salt or derivative thereof is not limited, but it is generally lower than 50° C.

Alternatively, the compounds represented by the formula (I) can be prepared by a known process comprising reacting an α-acylamino-α-arylacetamidecephalosporin represented by the formula (IV)

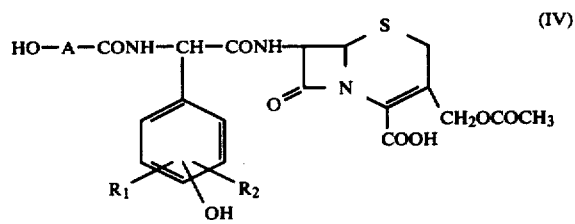

wherein HO-A-, $R_1$ and $R_2$ are as defined above, with a compound of the formulae

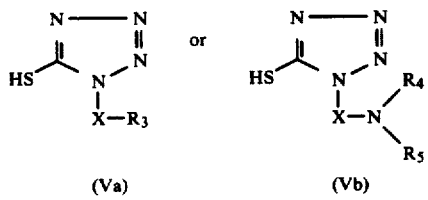

wherein $R_3$, $R_4$, $R_5$ and X are as defined above or a salt thereof. Such a known process is disclosed in, for example, Japanese Patent Publication Nos. 12136/71, 2340/71 and 14734/71, Japanese Patent Application (OPI) NO. 68593/73 (the term "OPI" as used herein refers to a "published unexamined Japanese patent application"), Journal of Chemical Society, 1965, p. 5015, Belgian Patent 864-459, etc.

Further, the compounds represented by the formula (I) can also be prepared by reacting an acylaminocarboxylic acid represented by the formula (IV)

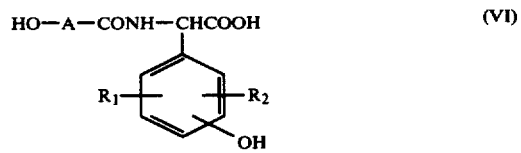

wherein A, $R_1$ and $R_2$ are as defined above, or a reactive derivative thereof, with a compound represented by the formula (VII)

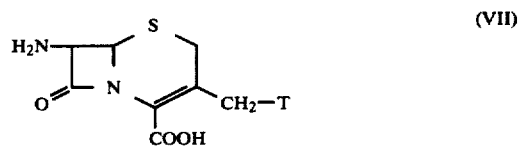

wherein T is as defined above, or a derivative thereof.

The reaction between the acylaminocarboxylic acid of the formula (VI) or a derivative thereof and the compound of the formula (VII) can be conducted in the same manner as described previously for the reaction between the compound (II) and the compound (III).

The present invention is further illustrated by the following Examples, but they are not to be construed as limiting the present invention. Unless otherwise indicated, all parts, percents and ratios are by weight.

EXAMPLE 1

Preparation of 7-[D-α-(4-hydroxy-6-methylpyridine-3-carboxyamido)-α-(4-hydroxyphenyl)acetamido]-3-(1-carboxymethyl-1H-tetrazol-5-ylthiomethyl)-3-cephem-4-carboxylic acid 8.8 g of a triethylamine salt of 7-[D-α-(4-hydroxy-6-methylpyridine-3-carboxyamido)-α-(4-hydroxyphenyl)acetamido]cephalosporanic acid, 2.36 g of sodium bicarbonate and 3.0 g of 1-carboxymethyl-5-mercapto-1H-tetrazole were added to 117 ml of a phosphate buffer solution (pH 6.0), and the resulting mixture was allowed to react at 50° C. for 16 hours and then at 60° C. for 3 hours with stirring. The reaction mixture was allowed to cool to room temperature and adjusted to pH 2.0 with 6 N hydrochloric acid. The precipitated crystals were collected by filtration and dried over phosphorus pentoxide under reduced pressure to afford 6.35 g of a crude product of the titled compound.

The crude product thus obtained was then subjected to liquid chromatography, and the fractions containing the desired product were collected, concentrated and precipitated with an acid by adjusting to pH 2.0 to afford a purified product. An equimolar amount of sodium bicarbonate was added to the above purified product and the mixture was freeze-dried to obtain a monosodium salt of the titled compound.

Melting Point, 257° C. (decomposition).

IR (KBr): 1760, 1660 cm$^{-1}$ $H^1$-NMR (90 MHz, $d_6$-DMSO): δ ppm (pattern, number of protons, assignment), 2.27 (s, 3H, C$\underline{H}_3$), 3.45 (broad, 2H, 2-C$\underline{H}_2$), 4.17 (broad, 2H, 3-C$\underline{H}_2$), 4.77 (s, 2H, >N—C$\underline{H}_2$—COO), 4.90 (d, 1H, 6-C$\underline{H}$—), 5.63 (dd, 1H, 7-C$\underline{H}$), 5.85

(d, 1H, —CONHC$\underline{H}$—CO—), 6.21 (s, 1H, 5-proton on pyridine ring), 6.6, 7.15 (d, 4H, proton on phenyl ring), 8.17 (s, 1H, 2-proton on pyridine ring), 9.17 (d, 1H, —CON$\underline{H}$—), 11.32 (d, —CON$\underline{H}$—).

EXAMPLE 2

The following compound was prepared according to the procedure as described in Example 1:

7-[D-α-(4-hydroxy-6-methylpyridine-3-carboxyamido)-α-(4-hydroxyphenyl)acetamido]-3-(1-sulfomethyl-1H-tetrazol-5-ylthiomethyl)-3-cephem-4-carboxylic acid monosodium salt.

Melting Point of 258° C. (decomposition).

IR (KBr): 1750, 1655 (cm$^{-1}$).

$H^1$-NMR (90 MHz, $d_6$-DMSO): δ ppm (pattern, number of protons, assignment), 2.33 (s, 3H, —C$\underline{H}_3$), 3.0–3.8 (broad, 2-C$\underline{H}_2$), 4.17 (broad, 2H, 3-C$\underline{H}_2$—S—), 4.94–4.97 (m, 2H, 6-C$\underline{H}$—, >N—C$\underline{H}_2$—SO$_3$—), 5.70 (dd, 1H, 7-C$\underline{H}$), 6.05 (d, 1H, —CONH—C$\underline{H}$—CONH—), 6.27 (s, 1H, 5-proton on pyridine ring), 6.60 (d, 2H, proton on phenyl ring), 7.15 (d, 2H, proton on phenyl ring), 8.17 (s, 1H, 2-proton on pyridine ring), 9.20 (d, 1H, —CONH—), 11.53 (d, 1H, —CONH—).

EXAMPLE 3

The following compound was prepared according to the procedure as described in Example 1:

7-[D-α-(4-hydroxy-6-methylpyridine-3-carboxyamido)-α-(4-hydroxyphenyl)acetamido]-3-(1-carboxyethyl-1H-tetrazol-5-ylthiomethyl)-3-cephem-4-carboxylic acid.

Melting Point, 143°–149° C. (decomposition).

H¹-NMR (d₆-DMSO, 60 MHz): δ ppm (pattern, number of protons, assignment), 2.27 (s, 3H, —CH₃), 2.93 (t, 2H, N—CH₂CH₂COOH), 3.62 (broad, 2H, 2-CH₂), 4.33 (m, >N—CH₂CH₂COOH), 4.97 (d, 1H, 6-CH), 5.67

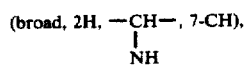

6.27 (s, 1H, 5-proton on pyridine ring), 6.83 (d, 2H, proton on phenyl ring), 7.27 (d, 2H, proton on phenyl ring), 8.27 (s, 1H, 2-proton on pyridine ring), 9.27 (d, 1H, —CONH—), 11.03 (d, 1H, —CONH—).

EXAMPLE 4

The following compound was prepared according to the procedure as described in Example 1:

7-[D-α-(4-hydroxy-6-methylpyridine-3-carboxyamido)-α-(4-hydroxyphenyl)acetamido]-3-(1-carboxypropyl-1H-tetrazol-5-ylthiomethyl)-3-cephem-4-carboxylic acid.

Melting Point, 182°–183° C. (decomposition).

H¹-NMR (60 MHz, d₆-DMSO): δ ppm (pattern, number of protons, assignment), 1.8–2.4 (m, 7H, —CH₃, >N—CH₂—C₂—), 3.63 (broad, 2H, 2-CH₂), 4.30 (broad, 4H, 3-CH₂, >N—CH₂CH₂—CH₂COOH), 4.98 (d, 1H, 6-CH—), 5.6–5.9

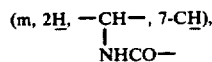

6.28 (s, 1H, 5-proton on pyridine ring), 6.73 (d, 2H, proton on phenyl ring), 7.27 (d, 2H, proton on phenyl ring), 8.30 (s, 1H, 2-proton on pyridine ring), 9.30 (d, 1H, —CONH—), 11.1 (d, 1H, —CONH—).

EXAMPLE 5

Preparation of 7-[D-α-(4-hydroxy-6-methylpyridine-3-carboxyamido)-α-(4-hydroxyphenyl)acetamido]-3-(1-dimethylaminoethyl-1H-tetrazol-5-ylthiomethyl)-3-cephem-4-carboxylic acid 8.14 g of triethylamine salt of 7-[D-α-(4-hydroxy-6-methylpyridine-3-carboxyamido)-α-(4-hydroxyphenyl)acetamido]cephalosporanic acid, 1.75 g of sodium bicarbonate and 3.0 g of 1-dimethylaminoethyl-5-mercapto-1H-tetrazole were added to 109 ml of a phosphate buffer solution (pH 6.0), and the resulting mixture was allowed to react at 50° C. for 16 hours and then at 60° C. for 3.5 hours with stirring. The reaction mixture was allowed to cool to room temperature and adjusted to pH 2.0 with 6 N hydrochloric acid. The precipitated crystals were filtered and dried over phosphorus pentoxide under reduced pressure to obtain 5.0 g of a crude product of the titled compound.

The crude product thus obtained was then subjected to liquid chromatography, and the fractions containing the desired product were collected, concentrated and precipitated with an acid by adjusting to pH 2.0 to obtain a purified product. An equimolar amount of sodium bicarbonate was added to the above purified product and the mixture was freeze-dried to obtain a sodium salt of the titled compound.

Melting Point, 252° C. (decomposition).

IR (KBr): 1760, 1660 cm⁻¹

H¹-NMR (90 MHz, d₆-DMSO): δ ppm (pattern, number of protons, assignment), 2.05

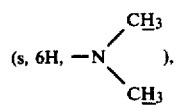

2.33 (s, 3H, methyl group on pyridine ring), 3–3.8 (overlapping with peak of water, 2-CH₂, —CH₂N<), 4–4.5 (m, >N—CH₂, 3—CH₂S—), 4.93 (d, 1H, 6-CH), 5.68 (dd, 1H, 7—CH), 6.1

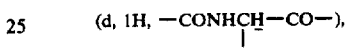

6.25 (s, 1H, 5-proton on pyridine ring), 6.51, 7.08 (d, proton on phenyl ring), 8.11 (s, 1H, 2-proton on pyridine ring), 9.13 (broad d, —CONH), 11.63 (broad d, —CONH).

Preparation of 7-[D-α-(4-hydroxy-6-methylpyridine-3-carboxyamido)-α-(4-hydroxyphenyl)acetamido]-3-(1-pyridinio)methyl-3-cephem-4-carboxylate A solution of 2.63 g of a triethylamine salt of 7-[D-α-(4-hydroxy-6-methylpyridine-3-carboxyamido)-α-(4-hydroxyphenyl)acetamido]cephalosporanic acid, 10 g of potassium thiocyanate and 0.481 g of pyridine in 10 ml of water was allowed to react at 58° to 60° C. for about 10 hours with stirring. The reaction mixture was allowed to cool to room temperature, 30 ml of water was added thereto and the insoluble substance formed was removed by filtration. The filtrate was adjusted to pH 2 with 2 N hydrochloric acid and, after stirring under ice-cooling, the precipitated crystals were filtered and dried on phosphorus pentoxide under reduced pressure to obtain 1.60 g of a crude product of the titled compound which was then purified by liquid chromatography.

H¹-NMR (60 MHz, d₆-DMSO: δ ppm (pattern, number of protons, assignment), 2.27 (s, 3H, —CH₃), 3.43 (broad, 2H, 2-CH₂—), 5.07 (d, 1H, 6-CH—), 5.40–5.97

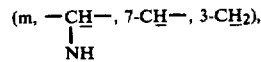

6.27 (s, 1H, 5-proton on pyridine ring), 6.70, 7.23 (d, 4H, proton on phenyl ring), 8.17 (m, 2H, 3-proton of pyridinium), 8.27 (s, 1H, 2-proton on pyridine ring), 8.58 (d, 1H, 4-proton of pyridinium), 9.02 (d, 2H, 2-proton of pyridinium), 9.28 (broad d, 1H, —CONH—), 11.02 (broad d, 1H, —CONH).

The following compound was prepared in the same procedures as above:

7-[D-α-(4-hydroxy-6-methylpyridine-3-carbox-yamido)-α-(4-hydroxyphenyl)acetamido]-3-(3-carboxy-1-pyridinio)methyl-3-cephem-4-carboxylate.

H¹-NMR (60 MHz, d₆-DMSO): δ ppm (pattern, number of protons, assignment), 2.25 (s, 3H, —CH₃), 3.42 (broad, 2H, 2-CH₂), 5.05 (d, 1H, 6-CH—), 5.3–6.0

(broad m, —CH—, 7-CH—, 3-CH₂),
    |
    NH 6.27 (s, 1H, 5-proton on pyridine ring), 6.70, 7.23 (m, 4H, proton on phenyl ring), 8.32 (m, 2H, 2-proton on pyridine ring, pyridinio proton), 8.67–9.67 (m, —CONH—, pyridinio proton), 11.07 (broad d, 1H, —CONH—).

7-[D-α-(4-hydroxy-6-methylpyridine-3-carbox-yamino)-α-(4-hydroxyphenyl)acetamido]-3-(4-carbam-oyl-1-pyridinio)methyl-3-cephem-4-carboxylate.

H¹-NMR (60 MHz, d₆-DMSO): δ ppm (pattern, number of protons, assignment), 2.27 (s, 3H, —CH₃), 3.45 (broad, 2H, 2-CH₂), 5.10 (d, 1H, 6-CH—), 5.27–6.13

(broad m, 7-CH, —CH—, 3-CH₂),
          |
          NH 6.30 (s, 1H, 5-proton on pyridine ring), 6.72, 7.25 (m, 4H, proton on phenyl ring), 8.30 (s, 1H, 2-proton on pyridine ring), 8.50 (d, 3-proton of pyridinio), 11.08 (d, 1H, —CONH).

7-[D-α-(4-hydroxy-6-methylpyridine-3-carbox-yamido)-α-(4-hydroxyphenyl)acetamido]-3-(4-carboxy-1-pyridinio)methyl-3-cephem-4-carboxylate.

H¹-NMR (90 MHz, d₆-DMSO): δ ppm (pattern, number of protons, assignment), 2.30 (s, 3H, —CH₃), 3.38 (broad, 2H, 2-CH₂), 5.03 (d, 1H, 6-CH), 5.2–6.0

(m, 4H, —CH—, 7-CH—, 3-CH₂),
        |
        NH 6.27 (s, 1H, 5-proton on pyridine ring), 6.68, 7.22 (m, 4H, proton on phenyl ring), 8.33 (s, 1H, 2-proton on pyridine ring), 8.43 (d, 2H, 3-proton of pyridinio), 9.25 (d, 2H, 2-proton of pyridinio), 11.08 (d, 1H, —CONH—).

Preparation of
7-[D-α-(4-hydroxylpyridine-3-carboxyamido)-α-(4-hydroxyphenyl)acetamido]cephalosporanic acid

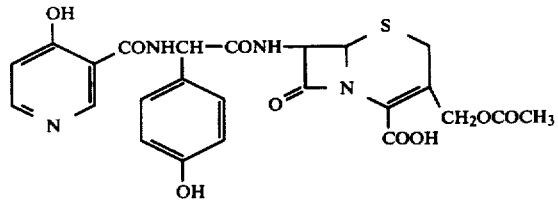

5 g of 7-[D-α-(p-methoxybenzyloxycarbonylamino)-α-(p-hydroxyphenyl)acetamido]cephalosporanic acid was added to a solution comprising 25 ml of trifluoroacetic acid and 2.5 ml of anisol under ice-cooling and stirring, and the mixture was stirred for 15 minutes. Then, the reaction mixture was added dropwise to 500 ml of diethyl ether while stirring. The precipitated crystals were collected by filtration, washed with diethyl ether, and dried over phosphorus pentoxide under reduced pressure to obtain 3.62 g of a trifluoroacetic acid salt of 7-[D-α-amino-α-(p-hydroxyphenyl)acetamido]-cephalosporanic acid. Then, 3.45 g of 7-[D-α-amino-α-(p-hydroxyphenyl)acetamido]cephalosporanic acid and 1.52 g of 4-hydroxypyridine-3-carboxylic acid N-hydroxysuccinimide ester were added to 21 ml of dimethyl sulfoxide, and 1.95 g of triethylamine was added dropwise thereto at room temperature. After allowing the mixture to react for 40 minutes with stirring, 115 ml of acetone was added to the resulting reaction mixture which was then stirred for 1 hour. After stirring the mixture for 30 minutes under ice-cooling, the precipitated crystals were collected by filtration, washed with acetone and dried over phosphorus pentoxide under reduced pressure to afford 3.14 g of a triethylamine salt of the titled compound.

Melting Point, 155°–157° C. (decomposition).

Preparation of
7-[D-α-(4-hydroxy-6-methylpyridine-3-carboxyamido)-α-(4-hydroxyphenyl)acetamido]cephalosporanic acid 21.96 g of anisol and 70.0 g of p-toluenesulfonic acid monohydrate were dissolved in 714 ml of acetonitrile, and 119 g of 7-[D-α-(p-methoxybenzyloxycarbonylamino)-α-(p-hydroxyphenyl)acetamido]cephalosporanic acid was added thereto, followed by allowing the mixture to react for 40 minutes with stirring. Thereafter, 238 ml of dimethyl sulfoxide and then 49.2 g of 4-hydroxy-6-methylpyridine-3-carboxylic acid N-hydroxysuccinimide ester were added to the reaction mixture at 10° C., and 82.3 g of triethylamine was added dropwise thereto at that temperature.

After completion of the addition, the resulting mixture was stirred at the same temperature for 40 minutes and then further allowed to react at 15° C. to 20° C. for one hour with stirring. 2 l of acetone was added dropwise to the reaction mixture for 10 minutes and the mixture was stirred at 18° C. for 30 minutes and then under ice-cooling for 1 hour. The crystals precipitated were collected by filtration, washed with 450 ml of acetone and dried over phosphorus pentoxide under reduced pressure to afford 95 g of a triethylamine salt of the titled compound.

Melting Point, 160°–173° C. (decomposition).

What is claimed is:

1. A compound of the formula

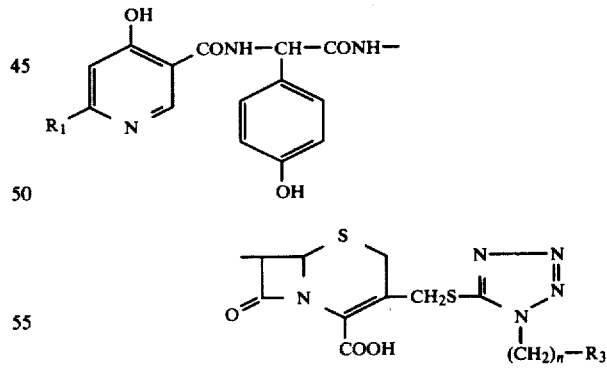

wherein R₁ is a methyl group, R₃ is a carboxyl group, and n is an integer of 1 to 4 and the pharmaceutically acceptable non-toxic salts thereof.

2. A compound of claim 1, which is 7-[D-α-(4-hydroxy-6-methylpyridine-3-carboxyamido)-α-(4-hydroxyphenyl)acetamido]-3-(1-carboxymethyl-1H-tetrazol-5-ylthiomethyl)-3-cephem-4-carboxylic acid.

3. An antimicrobial composition comprising an antimicrobially effective amount of the compound of claim 1, and a carrier or diluent.

* * * * *